(12) United States Patent
Fleury et al.

(10) Patent No.: US 8,042,382 B1
(45) Date of Patent: Oct. 25, 2011

(54) DEVICE FOR MEASURING PHYSICAL CHARACTERISTICS OF A POROUS SAMPLE

(75) Inventors: Marc Fleury, Domaine St François d'Assise (FR); Gabriel Ringot, Courbevoie (FR)

(73) Assignee: Institut Francais du Petrole, Cedex (FR)

( * ) Notice: Subject to any disclaimer, the term of this patent is extended or adjusted under 35 U.S.C. 154(b) by 0 days.

(21) Appl. No.: 09/083,180

(22) Filed: May 22, 1998

(30) Foreign Application Priority Data

May 23, 1997 (FR) ..................................... 97 06434

(51) Int. Cl.
*G01N 15/08* (2006.01)
(52) U.S. Cl. ............................................................ 73/38
(58) Field of Classification Search ................. 73/61.44, 73/61.43
See application file for complete search history.

(56) References Cited

U.S. PATENT DOCUMENTS

| | | | | |
|---|---|---|---|---|
| 3,693,435 A | * | 9/1972 | Cox et al. ................... | 73/861.04 |
| 3,762,211 A | * | 10/1973 | Poulsen ............................ | 73/38 |
| 4,316,174 A | * | 2/1982 | Sutton et al. ................... | 340/438 |
| 4,671,102 A | * | 6/1987 | Vinegar et al. ................. | 73/61.48 |
| 4,740,077 A | * | 4/1988 | Goodwill ......................... | 356/23 |
| 5,253,529 A | * | 10/1993 | Lenormand et al. ............ | 73/597 |
| 5,463,894 A | * | 11/1995 | Fleury et al. ...................... | 73/38 |
| 6,185,985 B1 | * | 2/2001 | Fleury et al. ...................... | 73/38 |
| 7,257,989 B2 | * | 8/2007 | Fleury .............................. | 73/38 |

* cited by examiner

*Primary Examiner* — Hezron E Williams
*Assistant Examiner* — Mark A Shabman
(74) *Attorney, Agent, or Firm* — Antonelli, Terry, Stout & Kraus, LLP.

(57) ABSTRACT

Device for measuring physical characteristics of a porous sample by performing successive drainage and imbibition phases in the presence of a first electricity-conducting fluid and of a second fluid of lower density than the first fluid, by means of a centrifuge whose speed is successively increasing and decreasing. The sample saturated with the first fluid is placed in a vessel (13) fastened to the end of an arm (9) driven in rotation by a motor (10) and communicating, by means of a rotating electro-hydraulic connector (17), with a stationary measuring signal control and acquisition unit (E) including hydraulic fluid displacement means and an acquisition device connected to a capacitive sonde in the vessel, which delivers signals indicative of the position of the interface between the two fluids. The device can be applied for analyzing rocks taken from an underground reservoir for example.

31 Claims, 4 Drawing Sheets

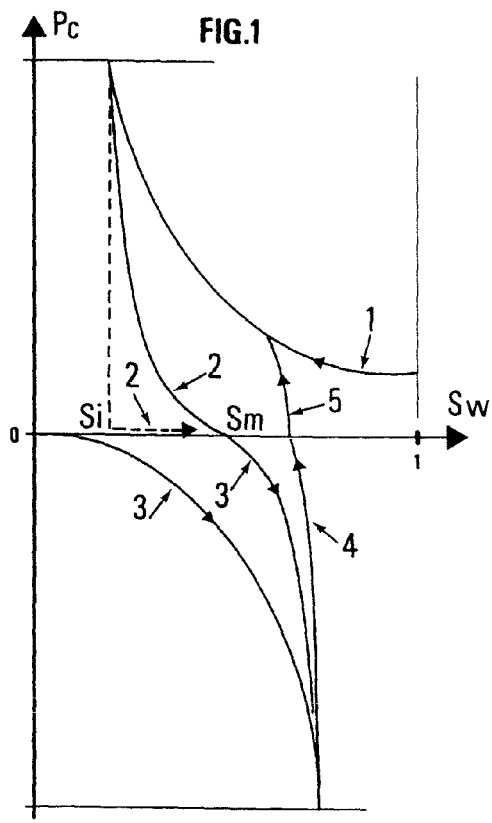
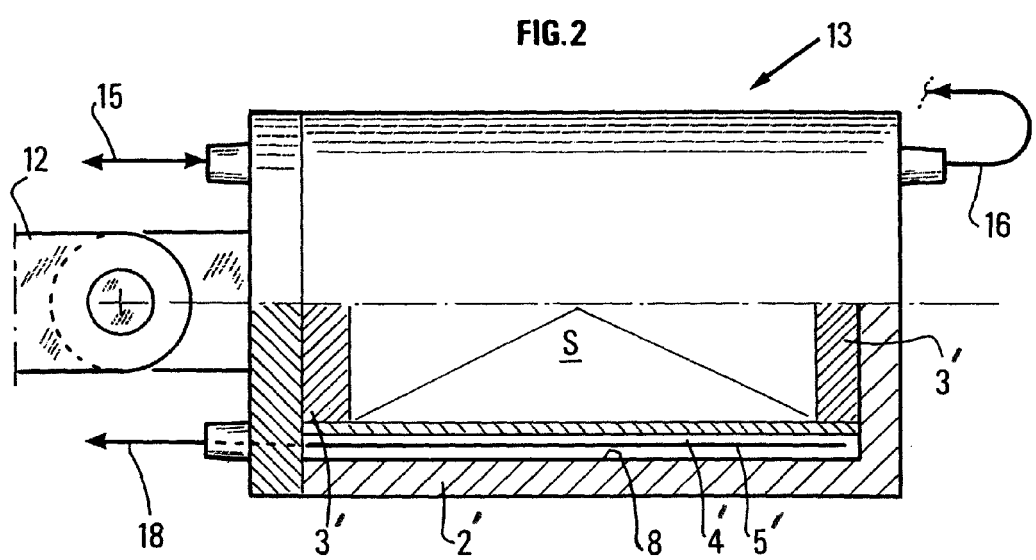

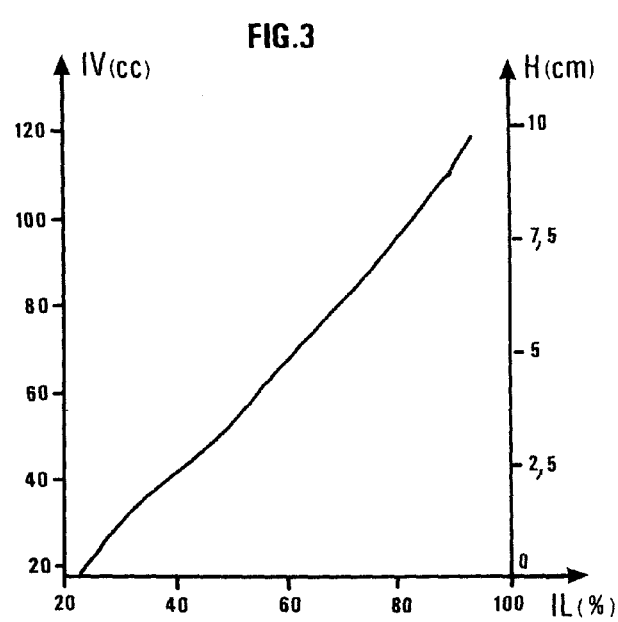
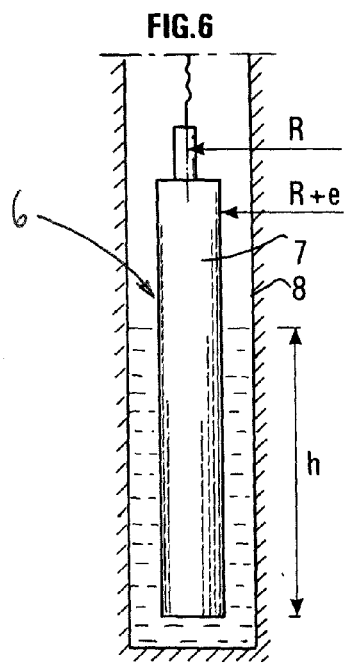
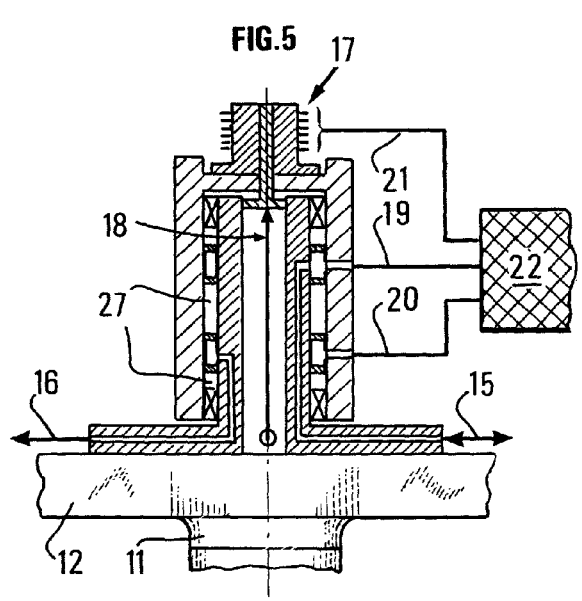
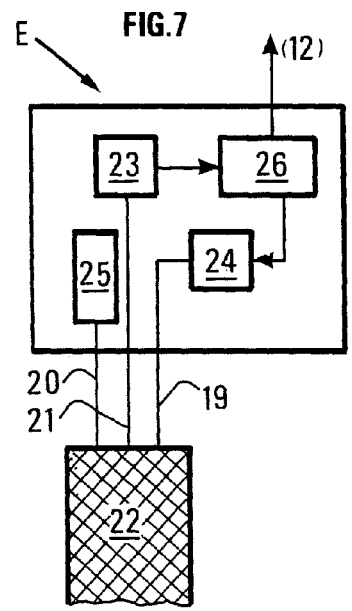

DEVICE FOR MEASURING PHYSICAL CHARACTERISTICS OF A POROUS SAMPLE

BACKGROUND OF THE INVENTION

1. Field of the Invention

The present invention relates to an improved device for measuring physical characteristics of a more or less porous sample. Such a device is notably well suited to test geologic samples and to determine various parameters such as the capillary pressure of rocks in drainage and imbibition phases, their wettability index, their relative permeability, their resistivity index, etc.

2. Description of the Prior Art

It is important to determine the wettability of rocks with respect to the water and to the oil which may be contained therein. To that effect, the rock must be subjected to a drainage process, that is a displacement of the fluids intended to decrease the water saturation thereof, followed by an imbibition, that is a displacement of the fluids allowing an increase of the water saturation (Sw) of the rock. The capillary pressure at one point is defined as the difference Pc at equilibrium between the pressure Po of the oil and the pressure Pw of the water. This parameter is meaningful only if the two fluids are in the continuous phase in the porous medium. For a water wet medium, only positive values are meaningful. On the other hand, if the medium has a mixed wettability, the fluids can remain in the continuous phase for the positive and for the negative capillary pressures (Pc) as well.

For an application of this type, a complete capillary pressure measuring cycle must therefore comprise (FIG. 1):

a) positive primary drainage of an initially 100% water-saturated sample (curve 1),
b) positive imbibition (curve 2),
c) negative imbibition (curve 3),
d) negative drainage (curve 4), and
e) positive secondary drainage (curve 5).

Knowledge of various parameters and notably of the wettability of rocks is useful notably when enhanced recovery is to be performed in a formation, by draining the effluents contained therein by injecting a fluid under pressure, and when the most suitable fluid (water or gas) for displacement of effluents is to be determined by means of preliminary tests.

French Patent A-0,603,040 filed by the assignee describes a method allowing measurement of physical characteristics of saturated rocks by subjecting them to a progressive-speed centrifugation and by measuring the amount of fluid displaced as a function of the rotating speed. The sample saturated with a liquid A for example is placed in an elongate container or vessel containing another fluid B of different density. The vessel is fastened to the end of a rotating arm and a centrifugal force is applied thereto so as to study the fluid displacements in the sample during at least two distinct phases. During a first drainage phase, the assembly is subjected to a centrifugal force applied along the length of the vessel so as to exert an expulsion force thereon, which tends to flow out of part of the first fluid B. At the same time, some of fluid A flows into the sample. The two fluids move through the sample until they reach a position of equilibrium where the force due to the capillary pressure in the pores compensates for the centrifugal force exerted.

It is well-known that the capillary pressure $P_C$ at a distance R from the fulcrum pin, when it is positive, is expressed by the following relation:

$$P_C(R) = \tfrac{1}{2}\Delta\rho\omega2(R^2_{max} - R^2) P_C(R_{max}) = 0$$

where $\omega$ is the angular rotating speed, $R_{max}$ is the distance from the base of the sample bar S to the fulcrum pin, and $\Delta\rho$ is the difference between the respective densities of the two fluids.

For negative values, the capillary pressure $P_C$ at a distance R from the fulcrum pin is:

$$P_C(R) = \tfrac{1}{2}\Delta\rho\omega^2(R^2_{min} - R^2) P_C(R_{min}) = 0.$$

During the re-imbibition phase (curve 2), the speed is decreased in order to study the re-integration of the initial fluid therein. With this type of method, local saturations are calculated by an inversion program from the total amount of water expelled from the sample.

The capillary pressure in the sample can be deduced from the precise measurement of the amount of initial fluid extracted as a function of the centrifugal force exerted and from the variation of the average fluid saturation $S_m$ of the sample as a function of the centrifugal force exerted, which is obtained, for example, by acoustic detection.

With a fluid-saturated sample, it can be seen (FIG. 1) that the saturation during the centrifugal drainage phase, for a determined radius r, decreases (curve 1) as the rotating speed w increases until a minimum value Si is reached. During this drainage phase, the rotating speed is increased in successive stages until a speed of 3500 rpm is reached for example. The fluid saturation variations are measured during the deceleration phase. A hysteresis phenomenon and a return, according to another variation curve (curve 2), to a relative maximum value Sm are observed during the re-imbibition phase of the porous material.

A system for maintaining the drained fluid in contact with the sample bar is preferably used so that, when the deceleration phase starts, the bar can be properly re-imbibed. To ensure this maintenance, the system stabilizes the interface level between the two fluids at a minimum level where it is level with the base of the bar, that is at the furthest distance from the fulcrum pin ($R_{max}$), at least throughout the deceleration phase.

Displacements inside the sample are followed either by measuring the variation of the time of flight of the ultrasounds through the sample, or by measuring the variation of the electric resistance thereof. The volume drained can be measured optically by a vessel provided with a transparent light and by observing the level variation by use of a stroboscopic lighting.

The fluids drained out of the sample can for example be transferred into a variable-volume chamber in the same vessel or in a second rotating vessel for example, by a pump borne by one of the arms and driven by an electric motor. Such a system is easy to implement and has a reasonable cost. However, it requires using a pump borne by the arm and therefore subjected to the centrifugal force. This is a drawback because it is difficult to find standard electric driving motors capable of withstanding the great accelerations required for implementation of the process, typically of the order of 3000 g. Special motors whose cost is very high must be used therefore.

SUMMARY OF THE INVENTION

The improved device according to the invention allows measurement of physical characteristics of a porous solid sample by performing successive drainage and imbibition phases, in the presence of a first electricity-conducting fluid and of a second fluid of lower density than the first fluid. It comprises a rotatably mobile equipment, including at least one elongate container or vessel provided with an inner cavity for the sample. The vessel is fastened to the end of an arm secured to a fulcrum pin and associated with balancing means and motive means intended for driving the arm in rotation and to create a centrifugal force exerted along the direction of elongation of the vessel.

The device finds applications notably in the petroleum domain for testing rocks which have been taken from reservoirs containing or likely to contain petroleum effluents.

The invention also finds applications in civil engineering for field hydrology purposes in order to evaluate the degree of pollution for example, or in the building industry in order to test construction materials allowing to select waterproofing treatments for example.

The device comprises a hydraulic system for forcing displacement of the fluids and means for detecting the position of the interface, externally connected to the detection means by a rotating connector, comprising a capacitive sonde placed in the vessel, along the direction of elongation thereof, in order to continuously follow the displacements of the interface between the two fluids in the vessel.

The capacitive sonde comprises for example a metallic rod coated with a thin layer of a dielectric material. It is connected to a device for measurement of the capacitance variation of the sonde in contact with the fluids in the vessel, resulting from the variation of the immersion thereof in the conducting fluid.

According to an embodiment, the device comprises a measuring and control system for controlling at least one fluid transfer so as to maintain the interface between the two fluids at a determined level in the vessel.

The measuring and control system is preferably stationary and connected to the vessel by connection means including a sealed rotating electro-hydraulic connector, hydraulic lines and electric linking means.

The system comprises for example a pump for the fluid having the lower density, a tank receiving at least part of the fluid expelled from the sample and a programmed microcomputer for acquisition of the signals delivered by the device and control of the fluid transfers, so as to maintain the interface between the two fluids at a constant level during operation.

The micro-computer preferably also comprises means for determining various physical parameters of the sample while taking into account the amounts of the two fluids displaced during operation.

According to an embodiment, the device comprises a rotating electro-hydraulic connector with two sealed hydraulic channels wherein a first channel is connected to the hydraulic system, the tank is stationary and is connected to the vessel by means of the second channel of the connector. Measurement of the content thereof allows corroboration of the measurement of the volume transferred by the pump.

According to another embodiment, the device comprises a rotating electro-hydraulic connector with two sealed hydraulic channels communicating the hydraulic system with two vessels arranged symmetrically and driven in rotation by the motive means wherein the tank is secured to the mobile equipment receiving fluid from the two vessels.

The measuring sonde which is used detects brine level variations with a good accuracy of the order of 0.02 cc.

The device according to the invention allows spontaneous imbibition of the sample which has been drained during a previous centrifugation phase and therefore allows detection with precision the opposite displacement of the interface between the two fluids during the next decrease phase until it is equal to zero. The characteristics thereof are very stable notably in relation to the rotating speed. The accuracy obtained by using the sonde for measuring the interface level between the two liquids is translated into an equal accuracy for the measurement of the saturation in the sample and it allows determination of the capillary pressure in the part of the bar between the interface and the face that is closest to the fulcrum pin. Furthermore, the sonde occupies a limited volume, which allows the size of the vessel to be reduced.

BRIEF DESCRIPTION OF THE DRAWINGS

Other features and advantages of the device according to the invention will be clear from reading the description hereafter of embodiments given by way of non limitative example, with reference to the accompanying drawings wherein:

FIG. 1 shows various curves representative of the saturation variations of a sample during a drainage-imbibition cycle;

FIG. 2 diagrammatically shows the inner layout of a vessel with its sonde allowing to follow the interface level between the two fluids;

FIG. 3 shows a variation example in percentage (IL) of the signal delivered by the measuring device as a function of the height H (and of the volume IV) of brine in the vessel;

FIG. 5 diagrammatically shows a cross-sectional view of the layout of an electro-hydraulic connector used to connect the vessel to an outer control and acquisition unit;

FIG. 6 illustrates the calculation of the sonde capacitance variation as a function of the level variation of the conducting liquid expelled from the sample during operation;

FIG. 7 shows the flowsheet of the external measuring signal control and acquisition assembly E.

DESCRIPTION OF THE PREFERRED EMBODIMENTS

First Embodiment

Figure 4:
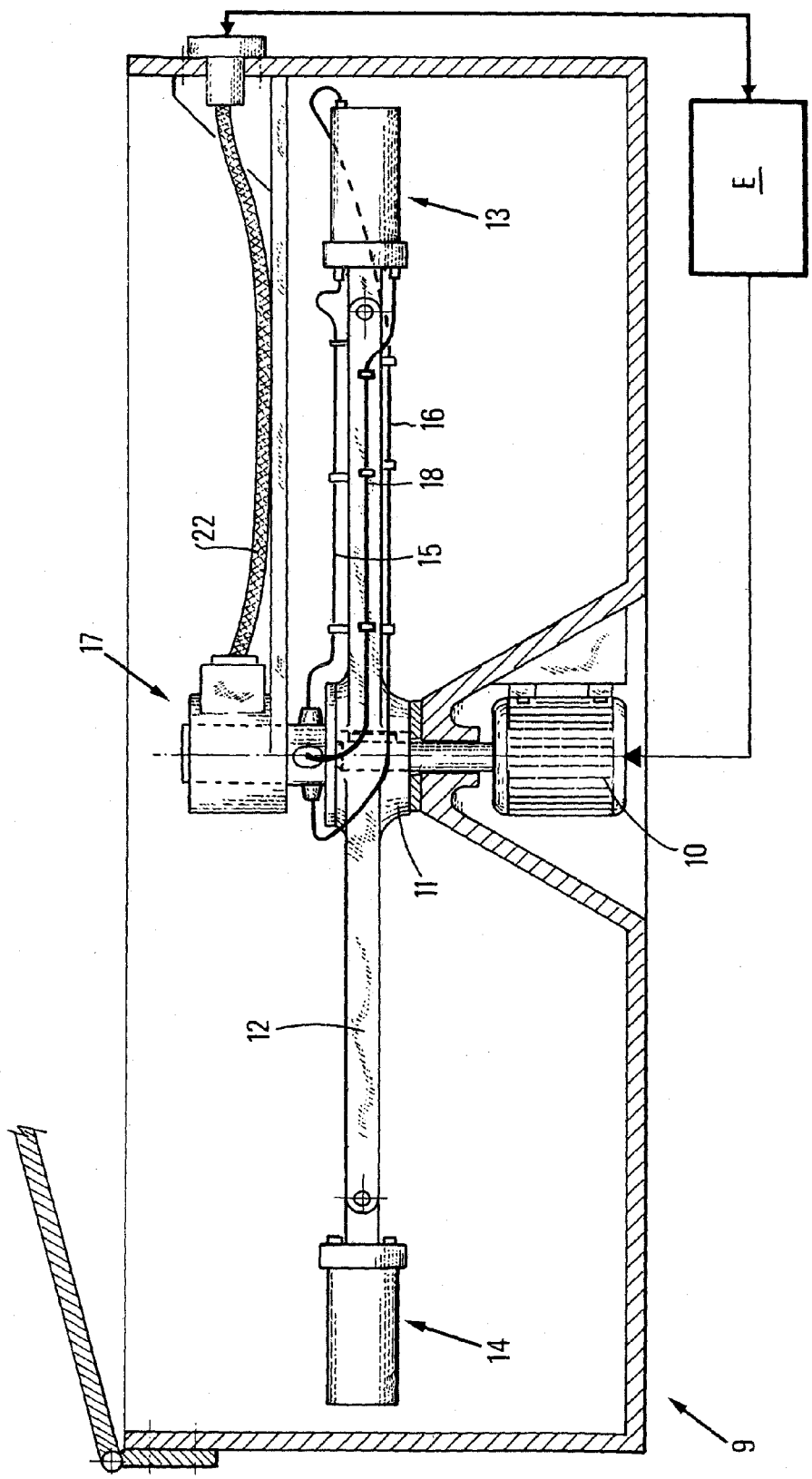
FIG. 4 diagrammatically shows the layout of a centrifuge and of the pumping means external to the rotating assembly.

The device according to the invention comprises (FIG. 2) an elongate container or vessel 2 intended for a porous rock sample S initially saturated with an electrically-conducting fluid A such as, for example, brine. Vessel 2' is initially filled with another, electrically insulating fluid B such as oil. At the opposite ends thereof, sample S in vessel 2' (FIG. 2) rests against two perforated disks 3' made, for example, from a porous ceramic. Vessel 2' also comprises a tubular lateral chamber 4', parallel to the longitudinal axis of the sample and of the vessel, for the capacitive type level detection sonde 5.

Sonde 5' comprises (FIG. 6) a first electrode 6 consisting of a metallic rod coated with a thin layer 7 of a dielectric material such as Teflon® or a glass ceramic for example, and a second bare metallic electrode 8 whose potential is used as a reference datum.

The inter-electrodes capacitance is expressed as follows:

$$c = 2\Pi\varepsilon_0\varepsilon_r\left[\ln\left(\frac{R+e}{R}\right)\right]^{-1} h \approx 2\Pi\varepsilon_0\varepsilon_r\frac{R}{e}h, \text{ where}$$

where
R is the radius of rod 6;
e is the thickness of the sheath or coating 7 covering the rod;
$\varepsilon_r$ is the relative dielectric constant of the material of the sheath;

$\epsilon_0$ is the dielectric constant of the vacuum whose value is 8.859 $10^{-12}$ A.s/V.m.

Any variation in the conducting fluid level in the vessel is translated into a capacitance variation of the sonde. When using an electrode with a 3-mm radius and a 0.05-mm seal coating, a sonde capacitance variation ranging between 10 and 1000 pF is for example obtained. Prior to use it, the sonde is calibrated by indicating to the associated measuring unit the minimum level (0%) and the maximum level (100%) between which the brine level can range in the vessel during operation. The response curve of the sonde as shown in FIG. 3 is thus established.

The centrifuge comprises a tank 9, an electric motor 10 whose shaft drives a hub 11 into rotation. Two identical arms 12 are mounted in opposition on hub 11. Two containers or vessels 13 and 14 are mounted to swivel at the ends of the two arms 12 so as to spontaneously line up with the direction of the applied centrifugal force, and balance each other in rotation. The sample to be measured is placed in vessel 13.

Two lines 15 and 16 are fastened along one of the arms 12 connect vessel 13 to a rotating electro-hydraulic connector 17 borne by hub 11. The first line 15 is used for injecting oil into vessel 13. The second line 16 is used for collecting the brine that is drained out of the sample through the rotation. A cable 18 connects measuring sonde 5 to rotating connector 17. By means of connector 17, the two rotating lines 15 and 16 communicate (FIG. 5) with two hydraulic lines 19 and 20. The conductors of cable 18 are electrically connected to another cable 21. These two lines and the cable form a linking element 22 between vessel 13 and an external assembly E.

This assembly comprises a measuring device 23 of a well-known type connected to cable 21 for delivering a signal proportional to the height of the sheathed electrode immersed in the conducting liquid. The section of the lateral chamber is known. An oil injection pump 24 is connected to line 19; a brine tank 25 is connected to line 20 and a control micro-computer 26 is provided with an interface card which is programmed to control pump 24 and the motor 10 of the centrifuge to provide acquisition of the measurements delivered by the measuring device.

In order to obtain a very high accuracy concerning fluid transfers, a pump 24 and a rotating connector 17 fitted with special seals with very limited leakage in a wide operating temperature range at pressures of the order of 0.5 MPa are selected.

Implementation

A sample saturated with brine for example is placed in the vessel and circuit 18 and 20 connecting the vessel to tank 25 is filled with brine. The centrifuge is operated at a minimum speed of 200 rpm. Oil is then pumped into the vessel via circuit 15 and 19 until the 0% minimum level corresponding to the position of the outer face of the sample for which sonde 5' has been calibrated is reached. The level of brine drained out of the sample gradually increases as the rotating speed of the centrifuge increases, for example, up to about 1000 rpm. The level of brine is measured by a level analyzer 23 (FIG. 7) and transmitted to computer 26 which controls the injection of oil under pressure in order to restore the initial 0% level. The brine is thus discharged through circuit 16 and 20 into tank 25 where the level rises.

When the rotating speed decreases (imbibition phase), oil pump 24 is actuated so as to recover just enough oil to maintain the level of the sonde at its 0% lower reference point. At the same time, the brine in tank 25 is recirculated to re-imbibe the sample.

The data acquired during the drainage-imbibition cycle are:

the volume of oil pumped into the vessel or out of it, which gives the average saturation of the sample;

the rotating speed which is related to the capillary pressure;

the position of the interface level in the vessel.

The average saturation of the sample can also be obtained from the level in brine tank 25 and from the position of the pump. The level variation in brine tank 25, which must confirm the noted volume of the oil pumped into the vessel, can also be optionally measured.

The micro-computer can also be programmed to perform directly computations of the petrophysical parameters deducible from the measurements performed during the drainage and imbibition cycles.

Other Embodiment

Figure 8:
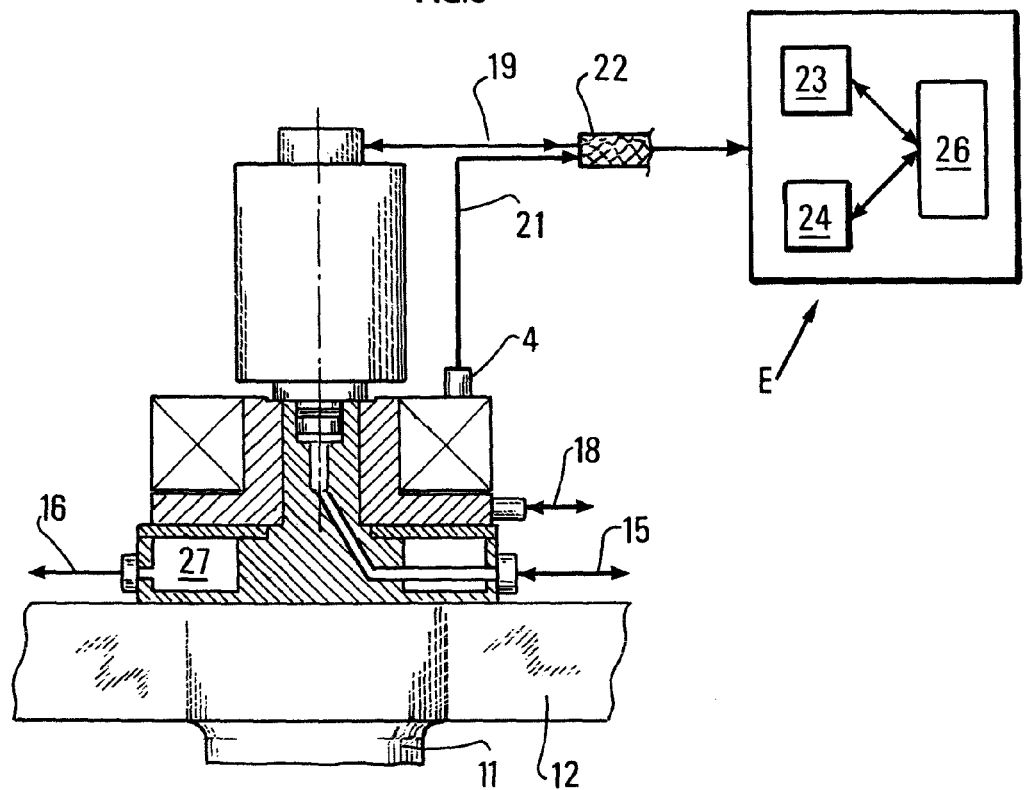
FIG. 8 shows another embodiment using a rotating electro-hydraulic connector with a single hydraulic circuit.

According to the embodiment schematized in FIG. 8, a rotating electro-hydraulic connector with a single hydraulic channel is used. Pump 24 in the external stationary assembly E delivers under pressure the less dense fluid by means of lines 15 and 19, connected to each other by rotating connector 17. Line 16 connects the end of the vessel which is at the furthest distance from the fulcrum pin to an auxiliary tank 27 also driven in rotation. This tank 27 is for example annular and is fastened to rotating hub 11.

According to an embodiment variant, tank 27 can also be an auxiliary cavity in the same vessel 13, as already described in the aforementioned French Patent A-2,603,040.

Implementation

The fluid produced (the denser or the less dense as the case may be) is maintained in contact with the sample during centrifugation. The expelled fluid can thus flow back into the sample when the imposed pressure decreases. According to the type of experimentation, the interface between the two fluids is maintained in contact with the sample at the first end thereof (at the furthest distance from the fulcrum pin) or at the opposite end (the closest to the fulcrum pin).

For negative capillary pressure values, the interface between the two fluids is maintained at a stable level close to the first end of the sample. Control of the position is provided by the measuring signal delivered by level analyzer 23 and the rotating speed is increased in stages for drainage and thereafter decreased in stages for a spontaneous imbibition.

On the other hand, for positive capillary pressure values, the interface between the two fluids is maintained close to the second end of the sample (the closest to the fulcrum pin) and the rotating speed is accelerated in stages for a forced imbibition.

As previously described, sample S is saturated, for example, with brine. The centrifuge is maintained at a minimum rotating speed (200 rpm for example). Oil is then injected into the vessel by means of pump 24 until the reference level is reached in the neighborhood of the first end, which can be monitored by means of the indications provided by capacitive sonde 5. The brine is expelled from the sample as the speed increases. In order to maintain the interface stability, oil under pressure is injected through line 15. The excess brine flows through line 16 into the tank.

On the other hand, for decreasing rotating speeds, the pump which is controlled by the capacitive sonde, draws oil to maintain the reference level selected for the interface and the brine accumulated in tank R flows back into vessel 13.

Once the minimum rotating speed restored, the interface level is positioned in the neighborhood of the second end of the sample (the closest to the fulcrum pin) and a forced imbibition phase can be started while maintaining this reference level as previously without having to take the sample out of the vessel.

The data acquired during the various phases are the volume of fluid pumped into or out of the vessel, which gives the average saturation of the sample, the rotating speed of the centrifuge, which gives the capillary pressure, and the position of the interface level.

In cases where the device comprises an electro-hydraulic connector with two hydraulic channels as shown in FIG. 5, tests can be carried out simultaneously on samples placed in the two symmetrical vessels 13 and 14. The brine simultaneously drained from the two vessels is collected in the same tank 27.

Results and Tests

The stability of the signal delivered by device 23 has been checked for the same brine level in the vessel in relation to three causes of instability: temperature variation, induced noise generated by the rotating contacts and other effects due to rotation. The results of the tests show that the measuring errors for the sonde are limited to less than 1% of the full scale, which gives a measurement to less than the nearest mm of the height of brine in the vessel.

An embodiment has been described (FIG. 8) wherein a rotating electro-hydraulic connector with a single hydraulic channel is used where the rotating part (rotor) is in the center of a stationary ring. However, a connector of a well-known type where the external ring is secured to hub 11 and mobile, and where the central part is stationary, can also be used without departing from the scope of the invention.

The invention claimed is:

1. An improved device for measuring physical characteristics of a porous solid sample by performing successive drainage and imbibition phases, in the presence of a first electrically-conducting fluid and of a second fluid of lower density than the first fluid comprising:
   rotatable mobile equipment including at least one elongate vessel provided with an inner cavity for the sample, the at least one vessel being fastened to an end of an arm secured to a fulcrum pin and associated with means for balancing, means for driving the arm in rotation for creating a centrifugal force exerted along a direction of elongation of the at least one vessel, a system for displacing at least the second fluid of lower density, and means for detecting an interface position of the fluids in the at least one vessel comprises a capacitive sonde placed in the at least one vessel along a direction of elongation thereof, for continuously detecting displacement of the interface between the two fluids in the at least one vessel, and the means for detecting an interface position of the fluids in the at least one vessel being externally connected to a measuring device through a rotatable connector.

2. A device as claimed in claim 1, wherein the capacitive sonde comprises a metallic rod coated with a layer of a dielectric material and connected to means for measuring the capacitance variation of the sonde in contact with the fluids in the at least one vessel resulting from the immersion thereof in the conducting fluid.

3. A device as claimed in claim 1, comprising a system for controlling at least transfer of one of the fluids in the at least one vessel to maintain the interface between the two fluids at a determined level in the at least one vessel.

4. A device as claimed in claim 2, comprising a system for controlling transfer of at least one of the fluids in the at least one vessel to maintain the interface between the two fluids at a determined level in the at least one vessel.

5. A device as claimed in claim 1, wherein the system is stationary and is connected to the at least one vessel by the rotatable connector including a sealed rotating electro-hydraulic connector, hydraulic lines and an electrical link and includes a pump for the fluid having the lower density, a tank for collecting at least part of the fluid expelled from the sample and a programmed micro-computer for acquiring signals from a means for measuring and controlling transfer of the fluids, to maintain the interface between the two fluids at a constant level during operation.

6. A device as claimed in claim 2, wherein the system is stationary and is connected to the at least one vessel by the rotatable connector including a sealed rotating electro-hydraulic connector, hydraulic lines and an electrical link and includes a pump for the fluid having the lower density, a tank for collecting at least part of the fluid expelled from the sample and a programmed micro-computer for acquiring signals from a means for measuring and controlling transfer of the fluids, to maintain the interface between the two fluids at a constant level during operation.

7. A device as claimed in claim 1, wherein the rotatable connector includes sealed hydraulic channels including a first channel for connection to a hydraulic system and a tank for collecting at least part of the fluid expelled from the sample and connected to the at least one vessel by a second channel of the rotatable connector.

8. A device as claimed in claim 2, wherein the rotatable connector includes sealed hydraulic channels including a first channel for connection to a hydraulic system and a tank for collecting at least part of the fluid expelled from the sample and connected to the at least one vessel by a second channel of the rotatable connector.

9. A device as claimed in claim 3, wherein the rotatable connector includes sealed hydraulic channels including a first channel for connection to a hydraulic system and a tank for collecting at least part of the fluid expelled from the sample and connected to the at least one vessel by a second channel of the rotatable connector.

10. A device as claimed in claim 4, wherein the rotatable connector includes sealed hydraulic channels including a first channel for connection to a hydraulic system and a tank for collecting at least part of the fluid expelled from the sample and connected to the at least one vessel by a second channel of the rotatable connector.

11. A device as claimed in claim 5, wherein the rotatable connector includes sealed hydraulic channels including a first channel for connection to a hydraulic system and a tank for collecting at least part of the fluid expelled from the sample and connected to the at least one vessel by a second channel of the rotatable connector.

12. A device as claimed in claim 1, comprising a rotating electro-hydraulic connector provided with at least one sealed hydraulic channel connected to the hydraulic system and a tank for collecting at least part of the fluid expelled from the sample which is secured to mobile equipment.

13. A device as claimed in claim 2, comprising a rotating electro-hydraulic connector provided with at least one sealed hydraulic channel connected to the hydraulic system and a tank for collecting at least part of the fluid expelled from the sample which is secured to mobile equipment.

14. A device as claimed in claim 3, comprising a rotating electro-hydraulic connector provided with at least one sealed hydraulic channel connected to the hydraulic system and a tank for collecting at least part of the fluid expelled from the sample which is secured to mobile equipment.

15. A device as claimed in claim 4, comprising a rotating electro-hydraulic connector provided with at least one sealed hydraulic channel connected to the hydraulic system and a tank for collecting at least part of the fluid expelled from the sample which is secured to mobile equipment.

16. A device as claimed in claim 1, wherein the rotatable connector is a rotating electro-hydraulic connector with sealed hydraulic channels communicating the hydraulic system, the at least one vessel is arranged symmetrically relative to the rotatable mobile equipment and is driven in rotation by the means for driving.

17. A device as claimed in claim 2, wherein the rotatable connector is a rotating electro-hydraulic connector with sealed hydraulic channels communicating the hydraulic system, the at least one vessel is arranged symmetrically relative to the rotatable mobile equipment and is driven in rotation by the means for driving.

18. A device as claimed in claim 3, wherein the rotatable connector is a rotating electro-hydraulic connector with sealed hydraulic channels communicating the hydraulic system, the at least one vessel is arranged symmetrically relative to the rotatable mobile equipment and is driven in rotation by the means for driving.

19. A device as claimed in claim 4, wherein the rotatable connector is a rotating electro-hydraulic connector with sealed hydraulic channels communicating the hydraulic system, the at least one vessel is arranged symmetrically relative to the rotatable mobile equipment and is driven in rotation by the means for driving.

20. A device as claimed in claim 5, wherein the rotatable connector is a rotating electro-hydraulic connector with sealed hydraulic channels communicating the hydraulic system, the at least one vessel is arranged symmetrically relative to the rotatable mobile equipment and is driven in rotation by the means for driving.

21. A device as claimed in claim 6, wherein the rotatable connector is a rotating electro-hydraulic connector with sealed hydraulic channels communicating the hydraulic system, the at least one vessel is arranged symmetrically relative to the rotatable mobile equipment and is driven in rotation by the means for driving.

22. A device as claimed in claim 1, comprising a measuring and control system for controlling at least one fluid transfer to maintain the interface between the fluids at a determined level in the at least one vessel including means for determining physical parameters of the sample by accounting for amounts of the fluids displaced during operation.

23. A device as claimed in claim 2, comprising a measuring and control system for controlling at least one fluid transfer to maintain the interface between the fluids at a determined level in the at least one vessel including means for determining physical parameters of the sample by accounting for amounts of the fluids displaced during operation.

24. A device as claimed in claim 3, comprising a measuring and control system for controlling at least one fluid transfer to maintain the interface between the fluids at a determined level in the at least one vessel including means for determining physical parameters of the sample by accounting for amounts of the fluids displaced during operation.

25. A device as claimed in claim 4, comprising a measuring and control system for controlling at least one fluid transfer to maintain the interface between the fluids at a determined level in the at least one vessel including means for determining physical parameters of the sample by accounting for amounts of the fluids displaced during operation.

26. A device as claimed in claim 1, including means for determining physical parameters of the sample by accounting for amounts of the fluids displaced during operation.

27. A device as claimed in claim 2, including means for determining physical parameters of the sample by accounting for amounts of the fluids displaced during operation.

28. A device as claimed in claim 3, including means for determining physical parameters of the sample by accounting for amounts of the fluids displaced during operation.

29. A device as claimed in claim 4, including means for determining physical parameters of the sample by accounting for amounts of the fluids displaced during operation.

30. A device as claimed in claim 5, including means for determining physical parameters of the sample by accounting for amounts of the fluids displaced during operation.

31. A device as claimed in claim 6, including means for determining physical parameters of the sample by accounting for amounts of the fluids displaced during operation.

\* \* \* \* \*